United States Patent [19]

Zentner

[11] Patent Number: 4,795,644
[45] Date of Patent: Jan. 3, 1989

[54] DEVICE FOR PH INDEPENDENT RELEASE OF DRUGS THROUGH THE DONNAN-LIKE INFLUENCE OF CHARGED INSOLUBLE RESINS

[75] Inventor: Gaylen M. Zentner, Lawrence, Kans.

[73] Assignee: Merck & Co., Inc., Rahway, N.J.

[21] Appl. No.: 81,090

[22] Filed: Aug. 3, 1987

[51] Int. Cl.⁴ .............................................. A61K 9/52
[52] U.S. Cl. ...................... 424/468; 424/457; 424/474; 424/482
[58] Field of Search ............... 424/469, 458, 473, 467, 424/438, 452, 453, 456, 454, 455, 457, 433, 468, 480, 428

[56] References Cited

U.S. PATENT DOCUMENTS

| | | | |
|---|---|---|---|
| 2,846,057 | 8/1958 | Polin | 260/0.5 |
| 2,928,770 | 3/1960 | Bardani | 126/42 |
| 3,538,214 | 11/1970 | Polli et al. | 260/0.5 |
| 3,957,523 | 5/1976 | Ohno et al. | 106/189 |
| 3,993,072 | 11/1976 | Zaffaroni | 424/430 |
| 4,160,452 | 7/1979 | Theeuwes | 424/427 |
| 4,200,098 | 4/1980 | Ayer et al. | 424/424 |
| 4,217,898 | 8/1980 | Theeuwes | 424/433 |
| 4,221,778 | 9/1980 | Raghamathan | 424/483 |
| 4,235,236 | 11/1980 | Theeuwes | 604/892.1 |
| 4,244,941 | 1/1981 | Lerk | 424/473 |
| 4,256,108 | 3/1981 | Theeuwes | 424/424 |
| 4,285,987 | 8/1985 | Ayer et al. | 427/3 |
| 4,309,996 | 1/1982 | Theeuwes | 604/892.1 |
| 4,320,759 | 3/1982 | Theeuwes | 604/892.1 |

OTHER PUBLICATIONS

J. Pharm. Sci., 72, pp. 772-775.

Primary Examiner—Thurman K. Page
Assistant Examiner—L. R. Horne
Attorney, Agent, or Firm—Joseph F. DiPrima; Michael C. Sudol

[57] ABSTRACT

A device is disclosed for the controlled delivery of a beneficial agent. The agent is delivered to the environment surrounding the device at a substantially constant rate for a specified period with a reduced dependence on the environmental pH. The device is comprised of a core compartment containing (1) a charged, water insoluble, non-diffusible component and (2) at least one diffusable water soluble ionizable beneficial agent. The core is surrounded by a water insoluble wall containing leachable pore forming additive(s) dispersed throughout said wall, with said wall impermeable to core components (1) and permeable to beneficial agent(s) (2). In operation the insoluble charged component (often polymeric resins) and water soluble ionizable beneficial agent have the same electro-static charge and do not form an ion exchange complex. Rather, a Donnan influenced mass transport phenomena of the beneficial agent is effected through the pores in the device, actuated by water from the environment, with migration of the freely mobile diffusible species (beneficial agent) away from the non-mobile species (charged entity). This effects the release of the beneficial agent through the wall at a controlled rate with reduced pH dependency.

22 Claims, 7 Drawing Sheets

DEVICE FOR PH INDEPENDENT RELEASE OF DRUGS THROUGH THE DONNAN-LIKE INFLUENCE OF CHARGED INSOLUBLE RESINS

FIELD OF THE INVENTION

This invention pertains to both a novel and useful drug delivery device for dispensing a beneficial agent, hereafter called "drug", to all regions of the gastrointestinal tract, regardless of the pH, at a controlled rate. The invention relates to a drug-delivery device comprising a core compartment that contains a charged, water insoluble, non-diffusible entity, herein called "charged resin", intimately mixed with a water-soluble, diffusible, ionized drug surrounded by a water insoluble porous wall. In operation the soluble drug and insoluble resin core components carry the same charge. The device delivers drug at a controlled rate in all regions of the gastrointestinal tract, which has a pH range generally from pH 1 to pH 8. The device thereby presents the beneficial agent to a variable environment of intended use at a controlled rate.

BACKGROUND OF THE INVENTION

The need for systems that can deliver a drug at a controlled rate to a variable environment (e.g. gastrointestinal tract) of use over a specified period of time is well established. The use of novel, charged, water-insoluble, non-diffusible resinous powders to modulate the pH dependency of drug release from osmotically sensitive devices with rate-controlling microporous walls that are permeable to both water and dissolved solutes has not been disclosed in the prior art and represents an advance in drug delivery technology and device composition. For example, devices for the controlled and continuous delivery of an active agent made from microporous materials are known to the prior art. Generally, the agent is embedded in or surrounded by the material and its release therefrom often is adversely influenced by external conditions. For example, U.S. Pat. No. 2,846,057 discloses a device consisting of a porous cellophane wall surrounding sodium fluoride that is released by water flowing into the pores to dissolve and leach it from the device. Controlled release is hard to obtain with this device because release is governed by external conditions and not by the device. That is, the amount of fluoride released changes with the rate of flow of water, with higher rates increasing the amount released, and lower rates decreasing the amount released over time. Similarly, U.S. Pat. No. 3,538,214 discloses a device consisting of drug coated with a film of water-insoluble plastic containing a modifying agent that is soluble at a certain pH. When this device is in the gastrointestinal tract, the modifying agent is partially or fully dissolved from the film by gastrointestinal fluid to form a porous film. This lets fluid through the film to dissolve the drug and leach it outwards through the pores into the tract. Controlled release is difficult to achieve with this device because the selection of the modifying agent is based on the unknown acid and alkaline state of the gastrointestinal tract which concomitantly influences pore formation and the exposure of drug to fluid. A similar device is disclosed in U.S. Pat. No. 2,928,770. The device of this patent consists of an outer layer of drug coated onto a porous material having its pores filled with a softened wax that is supposedly removed in the gastrointestinal tract by the alimentary fluid. This device cannot be relied on for controlled release because it too requires in situ pore formation which is dominated by unregulated external conditions and not by the device. The use of pore formers in substantially water impermeable polymers is disclosed in J. Pharm. Sci. 72, p. 772–775 and U.S. Pat. Nos. 4,244,941; 4,217,818; and 3,993,072. These devices release the core components by simple diffusion. U.S. Pat. No. 3,957,523 discloses a device which has a pH sensitive pore former in the device wall. U.S. Pat. Nos. 4,309,996; 4,320,759; 4,235,236 disclose layered devices with a microporous coating containing a drug layer and a swelling polymer layer acting as the driving force for delivery of agents. U.S. Pat. Nos. 4,256,108; 4,160,452; 4,200,098 and 4,285,987 disclose devices with pore formers in one of multiple wall layers. These devices contain a drilled hole for the release of core components through rate controlling semipermeable membranes that are substantially impermeable to dissolved drugs and other solutes. The use of charged resins to modulate drug release from the above devices was not disclosed. U.S. Pat. No. 4,221,778 discloses ion exchange resin drug complexes as delivery devices where the resin and drug carry opposite charges and microporous coats and osmotic factors are not included: drug release is actuated by exchange of the drug with another ion which dislodges the drug from the resin.

OBJECT OF THE INVENTION

Figure 1:
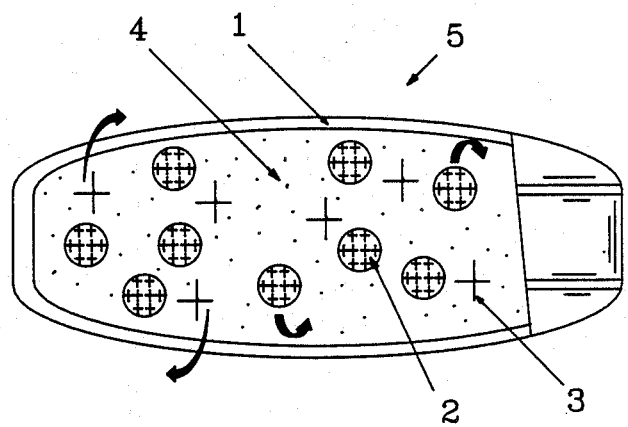
FIG. 1 is a schematic representation of the instant invention. The device, 5, has a core composition comprised of drug species, 3, charged resin(s), 2, and other excipients, 4, as needed to form a tablet suitable for the application of a microporous, rate-determining, water-insoluble wall, 1. As indicated by the bold arrows, in operation the insoluble resin, 2, will not permeate the wall, 1, whereas the dissolved drug species, 3, and excipients, 4, are freely permeable in response to osmotic and concentration gradients. in the intended environments of use, typically aqueous environments, the drug, 3, and resin, 2, carry the same electrostatic charge. These conditions impose Donnan effects onto the release behavior of the drug from the device as illustrated in FIG. 2. Conditions of electrical neutrality dictate an unequal distribution of permeable charged species across a coat that is impermeable to a charged resin. This phenomena favors the movement of drug bearing a like charge away from the resin, resulting in a modulation of the drug release normally associated with the mass transport effectuating concentration and osmotic gradients. Release rates of the devices of Examples 1–5 are shown in FIGS. 3–7, respectively

It is an immediate object of this invention to disclose a novel device for delivering drug to produce a beneficial effect. The device overcomes disadvantages associated with prior art devices through modulation of microporous wall release by charged, insoluble, resins bearing an electrostatic charge identical to that of the intended drug.

Another object of the invention is to provide a device for delivering drugs to all parts of the gastrointestinal tract at a substantially constant rate, regardless of the pH of the gastrointestinal tract, through a complex synergistic mechanism that incorporates aspects of Donnan-like electrostatics, diffusion, and osmosis.

Another object of the invention is to provide a drug delivery system that is readily manufacturable to deliver a pre-determined dose of a drug(s) at a programmed rate from compositions of matter in the varied geometries and sizes of tablets, pellets, multi-particulates, and such related dosage forms as familiar to those skilled in the art for oral, buccal, vaginal, rectal, nasal, ocular, aural, parenteral and related routes of administration.

Another object of the invention is to provide a drug delivery device for delivering drugs over a range of release rates as controlled by the device, and which device maintains its physical and chemical integrity throughout the release period.

Other objects, features and advantages of the invention will be apparent to those skilled in the art from the following detailed description of the invention taken in conjunction with the drawings and accompanying claims.

DETAILED DESCRIPTION OF THE INVENTION

The instant invention is directed to a drug-delivery device comprising: A. a core composition which comprises (a) a water insoluble, non-diffusible charged resin entity, (b) at least one diffusible water soluble ionizable drug carrying the same charge (+ or −) as component (a), and optionally, (c) other water soluble excipients, buffers, insoluble buffers, bulking agents, and osmotic regulators; and B. a water insoluble wall surrounding the core and prepared from (i) polymer materials that are permeable to water but substantially impermeable to solute and (ii) 0.1 to 75% by weight, based on the total weight of (i) and (ii), of at least one water leachable pore forming additive dispersed throughout said wall.

The expression water insoluble, non-diffusible charged resin entity as used herein broadly includes any electrostatically charged or electrostatically chargable species incapable of penetrating through the device wall. Representatives include: (a) cationic resins consisting of polystyrene, epoxy-amine, phenolic or condensate polymeric backbones with varying amounts of cross-linkage containing an active group of quaternary ammonium, secondary amine, tertiary amine in an aromatic matrix or tertiary amine in an aliphatic matrix. Examples include Dowex 1, Amberlite IRA-900, Dowex 2, Ionac A-550, and the like; (b) anionic resins with acrylic, methacrylic or phenolic polymeric backbones with phosphonic acid or carboxylic acid active groups such as Dowex CCR-1, Amberlite IRC-50, Zeo-Karb 226, and the like; (c) anionic resins with polystyrene or phenolic polymeric backbones with varying degrees of cross-linkage containing an active group of sulfonic acid such as Amberlite 200, Dowex 50, Duolite C-3, and the like. An extensive but not limiting list of charged resins can be found in the *Encyclopedia of Polymer Science and Technology*, Volume 7, pp. 692–742, Interscience Pub, Wiley and Sons, 1967.

Another group of charged resins that could be employed have cellulose as the principal support medium and include diethylaminoethyl cellulose, carboxymethyl cellulose, guanidoethyl cellulose, sulfoethyl cellulose, sulfopropyl cellulose and the like. An extensive but not limiting list of charged cellulosics can be found in *The Tools of Biochemistry*, Terrance G. Cooper, p. 143, Wiley and Sons, Inc., 1977.

Another type of charged resin entity includes the cross-linked vinyl pyridine polymers. At pH 6 or lower the vinylpyridine nitrogen protonates and thus assumes a positive charge. Other charged entities include charged silicates, charged clays, charged earths and zeolites.

The core compartment containing the water soluble drug and water insoluble charged resin as described herein is typically in the form of a solid conventional tablet, pellet or particulate. The core is completely encased by the porous wall. The core can be comprised of a mixture of agents combined to give the desired manufacturing and delivery characteristics. The number of agents that may be combined to make the core is substantially without an upper limit with the lower limit equalling two components. It may be useful to buffer the core compartment to keep the electrostatic charge of the drug the same as that of the charged resin.

The preferred specifications for the core are summarized below and include:

1. Core Drug Loading (size)-0.05 nanograms to 5 grams or more (includes dosage forms for humans and animals).

2. Osmotic pressure developed by a solution of the core-8 to 500 atmospheres, typically, with commonly encountered water soluble drugs and excipients; however osmotic pressures greater than zero are within guidelines.

3. Core solubility-continuous, uniform release (zero-order kinetics) of 90% or greater of the initially loaded core mass is theoretically predicted if the ratio of the dissolvable core mass solubility, S, to the dissolvable core mass density, $\rho$, that is $S/\rho$, is 0.1 or lower. Typically this occurs when 10% of the initially loaded dissolvable core mass saturates a volume of external fluid equal to the total volume of the initial dissolvable core mass.

$S/\rho$ ratios greater than 0.1 fall within the workings of the invention and result in lower percentages of initial core mass delivered under zero-order kinetics. $S/\rho$ can be selected to give acceptable combined characteristics of stability, release rate, and manufacturability.

4. Water insoluble charged resin component-0.01 to 75% by weight of the total core mass with a charge capacity of 0.01 to 50 mEq/g, preferably 0.01 to 15 mEq/g.

In cases where the drug has the desired solubility, osmotic pressure, density, stability, and manufacturability characteristics, there is no critical upper limit as to the amount that can be incorporated into a core mass and typically will follow the core loading (size) specification 1. The lower limit ratio of drug to excipient is dictated by the desired osmotic activity of the core composition, the desired time span and profile of release, and the pharmacological activity of the drug. Generally the core will contain 0.01% to 90% by weight or higher, of an active agent in mixture with another solute(s). Representative of compositions of matter that can be released from the device and can function as a solute are, without limitation, those compositions soluble in fluids inside the core compartment as described.

The expression drug as used herein broadly includes any compound, or mixture thereof, that can be delivered from the system to produce a beneficial result. The drug can be soluble in fluid that enters the reservoir and functions as an osmotically effective solute or it can have limited solubility in the fluid and be mixed with an osmotically effective solute(s) that is soluble in fluid that is delivered from the system. The term drug includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the term "drug" includes any physiologically or pharmacologicaloly active substances that produce a localized or systemic effect or effects in animals, which term includes mammals, humans and primates. The term also includes domestic household, sport or farm animals such as sheep, goats, cattle, horses and pigs, for administering the laboratory animals such as mice, rats and guinea pigs, and to fishes, to avians, to reptiles and zoo animals. The term "physiologically" as used herein denotes the administration of drug to produce normal levels and functions. The term "pharmacologically" denotes variations in response to amounts of drug including therapeutics, as defined in Stedman's Medical Dictionary, 1966, published by Williams & Wilkins, Baltimore, Md. The phrase drug formulation as used herein means the drug is in the compartment by itself, or the drug is in the compartment mixed with an osmotic solute, binder, dye, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, autocoid systems, alimentary and excretory systems, inhibitory or autocoids and histamine systems, and those materials that act on the central nervous system such as hypnotics and sedatives.

Examples of beneficial drugs are disclosed in *Remington's Pharmaceutical Sciences,* 16th Ed., 1980, published by Mack Publishing Co., Eaton, Pa.; and in *The Pharmacological Basis of Therapeutics,* by Goodman and Gilman, 6th Ed., 1980, published by the MacMillan Company, London; and in *The Merck Index,* 10th Edition, 1983, published by Merck % Co., Rahway, N.J. The dissolved drug can be in various forms, such as charged molecules, charged molecular complexes or ionizable salts. Acceptable salts include, but are not limited to hydrochlorides, hydrobromide, sulfate, laurylate, palmitate, phosphate, nitrate, borate, acetate, maleate, tartrate, oleate, salicylate, salts of metals, and amines or organic cations, for example quaternary ammonium.

Derivatives of drugs such as esters, ethers, and amides which have ionization and solubility characteristics suitable for use herein can be used alone or mixed with other drugs. Also, a drug that is water insoluble can be used in a form that is a water soluble ionizable derivative thereof to effectively serve as a solute, and on its release from the device, is converted by enzymes, hydrolyzed by body pH or other metabolic processes to the original form, or to a biologically active form.

Specific examples of drugs that may be adapted for use include pentobarbital sodium, phenobarbital, secobarbital, thiopental and mixtures thereof: heterocyclic hypnotics such as dioxopiperidines and glutarimides; hypnotics and sedatives such as amides and ureas, exemplified by diethylisovaleramide and $\alpha$-bromoisovaleryl urea; hypnotic and sedative urethanes and disulfanes; psychic energizers such as isocarboxazid, nialamide, phenelzine, imipramine, amitryptyline hydrochloride, tranylcypromine, pargylene, and protryptyline hydrochloride; tranquilizers such as chloropromazine, promazine, fluphenzaine, reserpine, deserpidine, and meprobamate; benzodiazepines such as diazepam and chlordiazepoxide; anticonvulsants such as primidone, phenytoin, and ethosuximide; muscle relaxants and antiparkinson agents such as mephenesin, methocarbomal, cyclobenzaprine hydrochloride, trihexylphenidyl hydrochloride, levodopa/carbidopa, and biperiden; antihypertensives such as $\alpha$-methyldopa and the pivaloyloxyethyl ester of $\alpha$-methyldopa; analgesics such as morphine sulfate, codeine sulfate, meperidine, and nalorphine; antipyretics and anti-inflammatory agents such as aspirin, indomethacin, sodium indomethacin trihydrate, salicylamide, naproxen, colchicine, feroprofen, sulindac, diflunisal, dichlofenac, indoprofen and sodium salicylamide; local anesthetics such as procaine, lidocaine, tetracaine and dibucaine; antispasmodics and muscle contractants such as atropine, scopolamine, methscopolamine, oxyphenonium, papaverine; prostaglandins such as $PGE_1$, $PGE_2$, $PGF_{2\alpha}$; antimicrobials and antiparasitic agents such as penicillin, tetracycline, oxytetracycline, chlorotetracycline, chloromphenicol, thiabendazole, ivermectin, and sulfonamides; antimalarials such as 4-aminoquinolines, 8-amino-quinolines and pyrimethamine; hormonal and steroidal agents such as dexamethasone, prednisolone, cortisone, cortisol and triamcinolone, androgenic steroids such as methyltestosterone; estrogenic steroids such as 17$\alpha$-estradiol, $\alpha$-estradiol, estriol, $\alpha$-estradiol 3-benzoate, and 17-ethynyl estradiol-3-methyl ether; progestational steroids such as progesterone; sympathomimetic drugs such as epinephrine, phenylpropanolamine hydrochloride, amphetamine, ephedrine and norepinephrine; hypotensive drugs such as hydralazine; cardiovascular drugs such as procainamide hydrochloride, amyl nitrite, nitroglycerin, dipyridamole, sodium nitrate and mannitol nitrate; diuretics such as chlorothiazide, acetazolamide, methazolamide, hydrochlorothiazide, amiloride hydrochloride and flumethiazide, sodium ethacrynate, and furosemide; antiparasitics such as bephenium, hydroxynaphthoate, dichlorophen and dapsone; antineoplastics such as mechlorethamine, uracil mustard, 5-fluorouracil, 6-thioguanine and procarbazine; $\beta$-blockers such as pindolol, propanolol, metoprolol, oxprenolol, timolol maleate, atenolol; hypoglycemic drugs such as insulin, isophane insulin, protamine zinc insulin suspension, global zinc insulin, extended insulin zinc suspension, tolubtamide, acetohexamide, tolazamide and chlorpropamide; antiulcer drugs such as cimetidine; nutritional agents such as ascorbic acid, niacin, nicotinamide, folic acid, choline, biotin, pantothenic acid; essential amino acids; essential fats; ophthalmic drugs such as timolol maleate, pilocarpine nitrate, pilocarpine hydrochloride, atropine sulfate, scopolamine; electrolytes such as calcium gluconate, calcium lactate, potassium chloride, potassium sulfate, sodium fluoride, ferrous lactate, ferrous gluconate, ferrous sulfate, ferrous fumurate and sodium lactate; and drugs that act on $\alpha$-adrenergic receptors such as clonidine hydrochloride.

Additional preferred drugs include quinoline and naphthyridine carboxylic acids and related compounds, such as norfloxacin.

Additional preferred drugs include budesonide, enprofylline, tranilast, albuterol, theophylline, aminophylline, brompheniramine, chlorpheniramine, promethazine, diphenhydramine, azatadine, cyproheptadine, terbutaline, metaproterenol, and isoproterenol; drugs which are antidepressants such as doxepin, trazodone; antipsychotic drugs such as haloperidol, thioridazine, trifluoperazine; sedative hypnotic and antianxiety drugs such as triazolam, temazepam, chlorazepate, alprazolam, diazepam, flurazepam, lorazepam, oxazepam, hydroxyzine, prazepam, meprobamate, butalbital, and chlorzoxazone; antiparkinson drugs such as benztropine and noxazinol; hormonal and steroidal drugs such as conjugated estrogens, diethylstilbesterol, hydroxy progesterone, medroxy progestrone, norethindrone, betamethasone, methylprednisolone, prenisone, thyroid hormone, and levothyroxine; antihypertensive and cardiovascular drugs such as isosorbide dinitrate, digoxin, nadolol, disopyramide, nifedipine, quinidine, lidocaine, diltiazem hydrochloride, verapamil, prazosin, captopril, enalapril, lisinopril, metyrosine, felodipine, tocainide, mexiletine, mecamylamine, and metyrosine; diuretic drugs such as spironolactone, chlorthalidone, metolazone, triamterene, methyclothiazide, and indacrinone; antiinflammatory drugs such as ibuprofen, ibuprofen lysinate, phenylbutazone, tolmetin, piroxicam, melclofenamate, auranofin, flurbiprofen and penicillamine; analgesic drugs such as acetaminophen, oxycodone, hydrocodone, and propoxyphene; antiinfective drugs such as cefoxitin, cefazolin, cefotaxime, cephalexin, nicarbazin, amprolium, ampicillin, amoxicillin, cefaclor, erythromycin, nitrofurantoin, minocycline, doxycycline, cefadroxil, miconazole, clotrimazole, phenazopyridine, clorsulon, fludalanine, pentizidone, cilastin, phosphonomycin, imipenem, arprinocid, and foscarnet; gastrointestinal drugs such as bethanechol, clidinium, dicyclomine, meclizine, proclorperizine, trimethobenzamide, loperamide, ranitidine, diphenoxylate, famotidine, metoclopramide and omeprazole; anticoagulant drugs such as warfarin, phenindione, and anisindione; and other drugs such as trientine, cambendazole, ronidazole, rafoxinide, dactinomycin, asparaginase, nalorphine, rifamycin, carbamezepine, metaraminol bitartrate, allopurinol, probenecid, diethylpropion, dihydrogenated ergot alkaloids, nystatin, pentazocine, phenylpropanolamine, phenylephrine, pseudoephedrine, trimethoprim, lovastatin, eptastatin, simvastatin, and ivermectin.

The above list of drugs is not meant to be exhaustive. Many other drugs will certainly work in the instant invention.

The drug can be in the core compartment as a solution, dispersion, paste, cream, particle, granule, emulsion, suspension or powder. Also, the drug can be mixed with a binder, dispersant, emulsifier or wetting agent and dyes.

The amount of drug, or drug admixed with other osmotically active solutes present in the device, is generally initially in excess of the amount that can be dissolved in the fluid that enters the reservoir. Under this physical state when the drug is in excess, the device will osmotically operate with Donnan-like modulation to give a substantially constant rate of relese. The drug release pattern can also be varied by having different amounts of drug in the reservoir to form solutions containing different concentrations of agent for delivery from the device. Generally, the device can house from 0.05 ng to 5 grams drug or more, with individual devices containing, for example, 25 ng, 1 mg, 5 mg, 250 mg, 500 mg, 1.5 g and the like.

Mixtures of drug with other pH modifying and/or osmotically active compounds may be used to attract fluid into the device producing a solution of compound which is delivered from the device, concomitantly transporting drug to the exterior of the device. Examples include but are not limited to magnesium sulfate, magnesium chloride, sodium chloride, lithium chloride, potassium sulfate, sodium carbonate, potassium carbonate, potassium bicarbonate, sodium sulfite, lithium sulfate, potassium chloride, calcium bicarbonate, sodium sulfate, sodium bicarbonate, sodium bitartrate, citric acid, adipic acid, potassium or sodium mono- or diphosphate, calcium lactate, d-mannitol, urea, inositol, sorbitol, pentaerythritol, magnesium succinate, magnesium oxide, magnesium hydroxide, tromethamine, tartaric acid, carbohydrates such as raffinose, sucrose, glucose, $\alpha$-d-lactose monohydrate, mixtures thereof and the like. The compound may be present in excess and it can be in any physical form such as particle, crystal, pellet, tablet, strip, film or granule.

The water insoluble, permeable rate controlling microporous wall as described herein, may be applied to core composition masses by spray coating procedures. The wall is comprised of (a) polymeric material that is insoluble in the fluids of the environment of intended use (usually water), (b) other added excipients that will dissolve in the environmental fluids or leach out of the wall. The leached wall is a sponge-like structure composed of numerous open and closed cells that form a discontinuous interwoven network of void spaces when viewed with a scanning electron microscope. This controlled porosity wall serves as both the water entry and core composition solution exit sites. The wall is permeable to both water and solutes, and as constituted in the environment of use has a small solute reflection coefficient, $\sigma$, and displays poor semipermeable characteristics when placed in a standard osmosis cell.

The specifications for the wall are summarized below and include:

1. Fluid Permeability of the wall: $6.96 \times 10^{-18}$ to $6.96 \times 10^{-14}$ cm$^3$ sec/g (equivalent to $10^{-5}$ to $10^{-1}$ cm$^3$ mil/cm$^2$ hr atm).

2. Reflection Coefficient: Microporous coats to have a reflection coefficient, $\sigma$, defined as:

$$\sigma = \frac{\text{osmotic volume flux} \times \text{hydrostatic pressure difference}}{\text{osmotic pressure difference} \times \text{hydrostatic volume flux}}$$

where $\sigma$ is less than 1, usually less than 0.8, preferrably less than 0.5 and most preferably less than 0.1.

Additional, preferred specifications for the wall include:

1. Plasticizers and Flux Regulating Additives: 0 to 50, preferably 0.001 to 50, parts per 100 parts wall material.

2. Surfactant Additives: 0 to 40, preferably 0.001 to 40, parts per 100 parts wall material.

3. Wall Thickness: 1 to 1,000, preferably 20 to 500, microns typically although thinner and thicker fall within the invention.

4. Microporous Nature: 5% to 95% pores between 10 angstroms and 100 microns diameter.

5. Pore Forming Additives: 0.1 to 75%, preferably 0.1 to 50%, by weight, based on the total weight of pore forming aditive and polymer, pore forming additive, preferably: (a) 0.1 to 50%, preferably 0.1 to 40%, by weight solid additive; (b) 0.1 to 40% by weight liquid additive, but no more than 75% total pore formers.

The water insoluble wall of the instant invention must not be covered on its inner or outer surface by a layer of material that is impermeable to dissolved solutes within the core during the period of operation.

Any polymer permeable to water but impermeable to solutes as previously defined may be used. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having an acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydroylsis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield ester containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose riacetate beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethy cellulose hydroxylated ethylenevinylacetate, poly(ortho ester)s, polyacetals, semipermeable polyglycolic or polylactic acid and derivatives thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, polyacrylate and polymethacrylate polymers, and derivatives and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,055; 3,541,006; and 3,546,142.

A controlled porosity wall can be generically described as having a sponge-like appearance. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the turtuosity of the microporous path and the porosity which relates to the size and number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used.

Pore forming additives may be used in the instant invention. The microporous wall may be formed in situ, by a pore-former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like; the alkaline earth metal salts such as calcium chloride, calcium nitrate, and the like; the transition metal salts such as fabric chloride, ferrous sulfate, zinc sulfate, cupric chloride, and the like. Water may be used as the pore-former. The pore-formers include organic compounds such as tromethamine, dimethyl sulfone, nicotinamide, saccharides and amino acids. The saccharides include the sugars sucrose, glucose, fructose, mannose, galactose, aldohexose, altrose, talose, lactose, monosaccharides, disaccharides, and water soluble polysaccharides. Also, sorbitol, pentaerythritol, mannitol, organic aliphatic and aromatic ols, including diols and polyols, as exemplified by polyhydric alcohols, poly(alkylene glycols), polyglycols, alkylene glycols, poly($\alpha$-$\omega$)alkyolenediols esters or alkylene glycols, polyvinylalcohol, poly vinyl pyrrolidone, and water soluble polymeric materials. Pores may also be formed in the wall by the volatilization of components in a polymer solution or by chemical reactions in a polymer solution which evolve gases prior to application or during application of the solution to the core mass resulting in the creating of polymer foams serving as the porous wall of the invention. The pore-formers are nontoxic, and on their removal channels are formed that fill with fluid. The channels become a transport path for fluid. In a preferred embodiment, the non-toxic pore-forming agents are selected from the group consisting of water soluble inorganic and organic compounds and salts, carbohydrates, polyalkylene glycols, poly($\alpha$-$\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes: A Structural Perspective*, 2nd Ed., by R. E. Kesting, Chapters 7 and 8, 1985, published by John Wiley & Sons, Inc.; *Chemical Reviews*, Ultrafiltration, Vol. 18, pages 373 to 455, 1934; *Polymer Eng. and Sci.*, Vol. 11, No. 4, pages 284 to 288, 1971, *J. Appl. Poly. Sci.*, Vol. 15, pages 811 to 829, 1971, and in U.S. Pat. Nos. 3,565,259; 3,615,024; 3,751,536; 3,801,692; 3,852,224; and 3,849,528.

It is generally desirable from a preparation standpoint to mix the polymer in a solvent. Exemplary solvents suitable for manufacturing the wall of the instant device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl ethyl ketone, methyl propyl ketone, n-hexane, ethyl lactae, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone-methanol (80:20), acetone-ethanol (90:10), methylene dichloride-methanol (80:20), ethyl acetate-ethanol (80:20), ethylene dichloride-methanol (80:20), methylene dichloride-methanol (50:50), methylene dichloride-methanol (78:22), acetone-water (90:10), chloroform-ethanol (80:20), methylene dichloride-ethanol (79:21), methylene chloride-methanol-water (15:10:1), carbontetrachloride-methanol (70:30), expressed as (weight:weight), and the like.

Exemplary plasticizers suitable for the present purpose include plasticizers that lower the temperature of the second-order phase transition of the wall or the elastic modulus thereof, and also increase the workability of the wall and its flexibility. Plasticizers may increase or decrease the permeability of the wall to fluids including water and aqueous solutions. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, dioctyl phthalate, di-(2-ethyl-hexyl)-phthalate, di-isopropyl phthalate, diamyl phthalate and dicapryl phthalate; alkyl and aryl phosphates such as triethyl phosphate, tributyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methyoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol dibutyrate and triethylene glycol dipropionate. Other plasticizers include polyethylene glycol 400, polyethylene glycol 20,000, camphor, N-ethyl-(o- and p-toluene)sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their tendency to remain in the plasticized wall, impart flexibility to the material and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\chi$, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the other wall forming materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability (flux) through the wall. The agent can be preselected to increase or decrease the fluid flux. Agents that produce a marked increase in permeability to a fluid such as water, are often essentially hydrophilic, while those that produce a marked decrease in permeability to fluids such as water, are often essentially hydrophobic. The flux regulators in some embodiments also can increase the flexibility and porosity of the lamina. Examples of flux regulators include polyhydric alcohols and derivatives thereof, such as polyalkylene glycols of the formula H—(O—alkylene)$_n$—OH wherein the bivalent alkylene radical is straight or branched chain and has from 1 to 10 carbon atoms and n is 1 to 500 or higher. Typical glycols include polyethylene glycols 300, 400, 500, 1500, 1540, 4000 and 6000 of the formula H—(OCH$_2$CH$_2$)$_n$—OH wherein n is typically 5 to 5.7, 8.2 to 9.1, 12.5 to 13.9, 29 to 36, 29.8 to 37, 68 to 84, and 158 to 204, respectively. Other polyglycols include the low molecular weight glycols of polypropylene, polybutylene and polyamylene.

Additional flux regulators include poly($\alpha,\omega$)alkylenediols wherein the alkylene is straight or branched chain of from 2 to 10 carbon atoms such as poly(1,3)-propanediol, poly(1,4)butanediol, poly(1,5)pentanediol and poly(1,6)hexanediol. The diols also include aliphatic diols of the formula HOC$_n$H$_{2n}$OH wherein n is from 2 to 10 and diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene—O)-$_n$—H wherein the divalent alkylene radical includes the straight chain groups and the isomeric forms thereof having from 2 to 6 carbons and n is 1 to 14. The esters and polyesters are formed by reacting the glycol with either a monobasic or dibasic acid or anhydride. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present purpose are those surfactants, when added to a wall forming material and other materials, aid in producing an integral composite that is useful for making the operative wall of a device. The surfactants act by regulating the surface energy of materials to improve their blending into the composite. The composite material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric. The anionic surfactants include sulfated, sulfonated, or carboxylated esters, amides, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quaternary alkylammonium salts, acylated polyamines, and salts of heterocyclic amines. Nonionic surfactants are typically esters and ethers of polyoxyalkylene glycols, polyhydric alcohols, or phenols. Poloxamers are included as nonionic surfactants. Ampholytic molecules such as betaine are also surfactants. Surfactants are discussed in *Surfactant Systems, Their Chemistry, Pharmacy, and Biology*, D. Attwood and A. T. Florence, Chapman and Hall Pub. Co., 1983, pgs 1–8.

Examples of surfactants include potassium laurate, sodium dodecyl sulfate, hexadecylsulphonic acid, sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, Igepal, sorbitan esters (Spans), polysorbates (Tweens), Triton-X analogs, Brij analogs, Myrj analogs, pluronics, tetronics, surface active drug agents such as phenothiazines and tricyclic antidepressants, and the like.

Suitable surfactants can be selected from the above and from other surfactants for blending with wall forming materials by using the surfactant's hydrophile-lipophile balance number, HLB. This number represents the proportion between the weight percentages of hydrophilic and lipophilic groups in a surfactant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known HLB number, blending it with the materials and observing the results. A uniform composite is formed with the correct HLB number, while a non-uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences*, 16th Ed., Mack Pub. Co., (1980), pages 316–319. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

The following examples illustrate the preparation of the drug-delivery devices of this invention and their controlled release of one or more therapeutically active ingredients into an environment of use and as such are not to be considered as limiting the invention set forth in the claims appended hereto.

EXAMPLES

In the following examples diltiazem hydrochloride was used as the model drug. The pKa of diltiazem hydrochloride is 7.7. In the devices described below the core compartment was buffered to keep the pH below 6 to keep diltiazem and the resins positively charged.

Example 1

A plurality of drug delivery systems containing Dowex 1 (8% cross-linked, 200-400 mesh) as a positively charged (quaternary ammonium) resin were prepared as follows: a wet granulation was made containing diltiazem hydrochloride, pentaerythritol, Dowex 1, citric acid, and adipic acid mixed 2:10:4:1:1, respectively. 10% w/w polyvinylpyrrolidone (29-32K) was used as a binder. Core tablets were prepared by compressing 600 mg aliquots (60 mg drug load) of the dried granulation into a 5/16" standard concave tabletting die by applying a 2 ton force with a single station hydraulic press. Next, the microporous wall was applied to these cores. 36 g cellulose acetate having an acetyl content of 32% and 36 g cellulose acetate having an acetyl content of 39% were dissolved in a dichloromethane/methanol solvent blend. To this was added 36 g sorbitol as pore former and 20 g polyethylene glycol 400 as a flux enhancer/plasticizer dissolved in a water/methanol solvent blend. The composite solution contained water:methanol:dichloromethane in an approximate 1:10:15 ratio. This solution was sprayed onto the cores in a commercial Uni-Glatt fluidized bed coating machine. A wall weighing 100 mg was applied.

Figure 3:
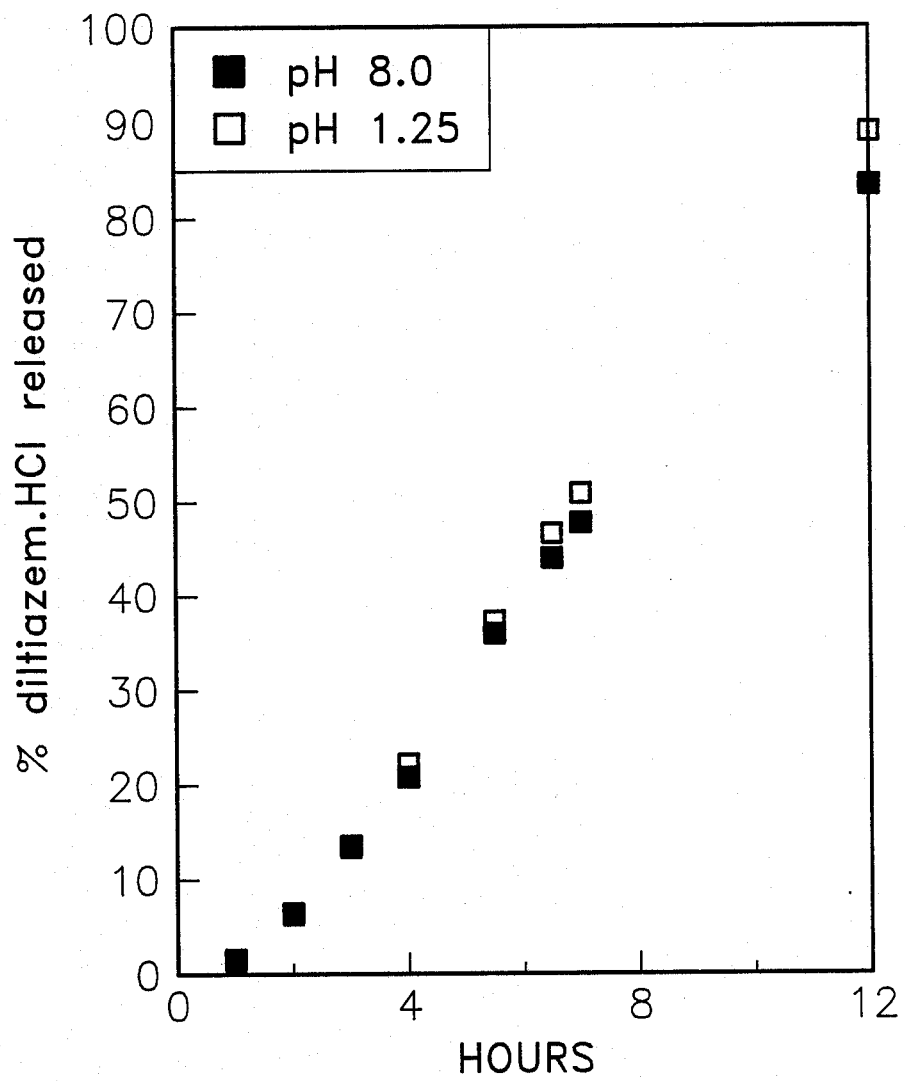

The diltiazem hydrochloride release from these devices in vitro into 900 ml volumes of 37° C., pH 1.2 HCl buffer and pH 8.0 phosphate buffer, both made isotonic with NaCl, was monitored in a USP Dissolution Method #2 apparatus with constant stirring at 50 rpm. HPLC was used to assay for diltiazem. The average release rates at both pH's are shown in FIG. 3. The rates of release were constant following a brief lag period and were independent of the pH surrounding the device.

Example 2

A plurality of drug delivery devices were prepared that contained no charged resin. A wet granulation was made containing diltiazem hydrochloride, pentaerythritol, citric acid, and adipic acid mixed 2:10:1:1, respectively with 10% w/w polyvinylpyrrolidone (29-32K) added as a binder. Core compartments were prepared by compressing 462 mg (60 mg drug load) of the dried granules in a 5/16" standard concave tabletting die as in Example 1. Next, the microporous wall was applied to these cores. 72 g cellulose acetate having an acetyl content of 39% was dissolved in a dichloromethane/methanol solvent blend. To this was added 54 g nicotinamide as pore former and 40 g polyethylene glycol 400 as flux enhancer/plasticizer dissolved in methanol. The composite solution contained dichloromethane:methanol in a 1.14:1 ratio. This solution was sprayed onto the cores in a commercial Uni-Glatt fluidized bed coating machine. A 410 micron thick wall was applied.

The in vitro release of diltiazem hydrochloride was monitored as in Example 1. The release rates in the absence of a positively charged resin were markedly dependent on the pH of the environment (see FIG. 4).

Example 3

A plurality of drug delivery devices were prepared with diltiazem HCl and the positively charged insoluble resin poly-4-vinylpyridine hydrochloride. The vinylpyridine nitrogen becomes protonated, and thus positively charged, at pH 6 or less. Citric acid and adipic acid were incorporated into the core compartment to maintain the pH below 6 inside the core compartment during operation, thus maintaining both the resin and drug in the positively charged state. A wet granulation was made containing 11% w/w diltiazem hydrochloride, 56% w/w pentaerythritol, 10% w/w poly-4-vinylpyridine hydrochloride, 6.5% w/w citric acid, 6.5% w/w adipic acid and 10% w/w polyvinylpyrrolidone (29-32K). Core compartments were prepared by compressing 540 mg aliquots (60 mg drug load) of the dried granules into a 5/16- standard concave tabletting die as in Example 1. Next, the microporous wall was applied to these core compartments. A coating solution identical to that of Example 2 was applied as in Example 2. A 410 micron thick wall was applied.

Figure 5:
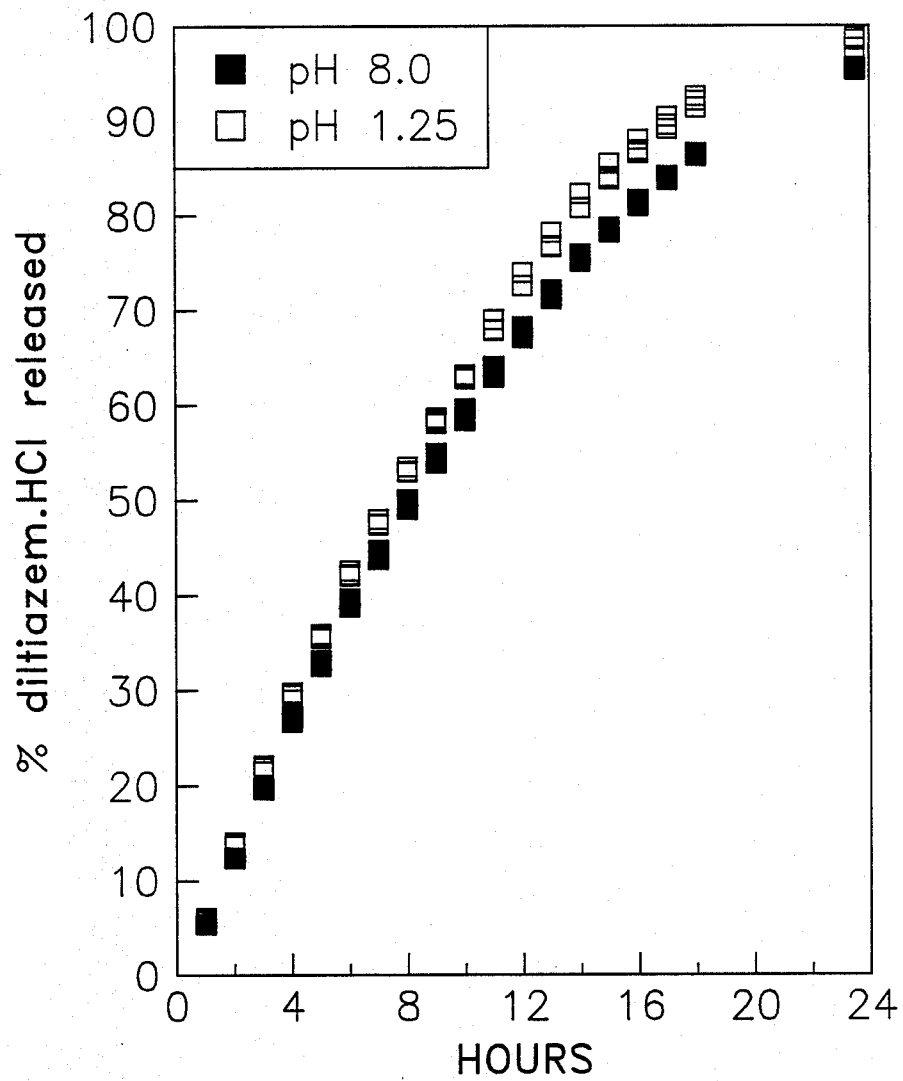

The diltiazem hydrochloride in vitro release was monitored as in Example 1. The release profiles of diltiazem HCl into pH 1.25 and pH 8.00 buffer solutions were essentially identical and independent of pH as shown in FIG. 5. The incorporation of the positively charged insoluble poly-4-vinylpyridine resin was obviated the pH dependence of the release of diltiazem hydrochloride noted in Example 2.

Example 4

A plurality of drug delivery devices were prepared with diltiazem HCl and the positively charged insoluble resin poly-4-vinylpyrridine hydrochloride. A wet granulation was made containing 9.5% w/w diltiazem hydrochloride, 48% w/w pentaerythritol, 21% w/w poly-4-vinylpyridine hydrochloride, 5.5% citric acid, 5.5% w/w adipic acid and 10.5% w/w polyvinylpyrrolidone (29-32K). Core compartments were made by compressing 636 mg aliquots (60 mg drug load) of the dried granules into a 5/16" standard concave tabletting die as in Example 1. Next, the microporous wall was applied. A coating solution identical to that of Example 2 was applied to the core compartments as in Example 2. A 420 micron thick wall was applied.

Figure 6:
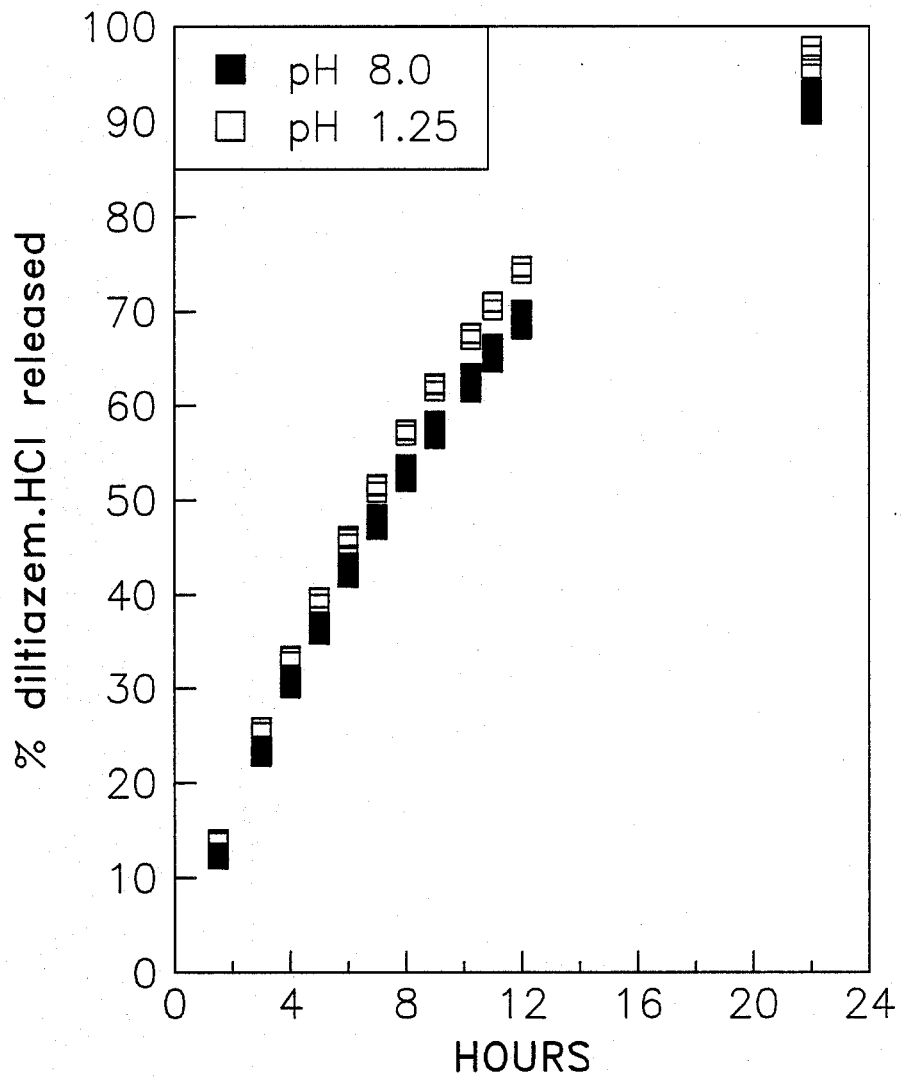

The diltiazem hydrochloride release was monitored as in Example 1. The release profiles of diltiazem HCl into pH 1.25 and pH 8.01 buffer solutions were essentially identical and independent of pH as shown in FIG. 6. The incorporation of the positively charged insoluble poly-4-vinylpyridine resin at a higher level than in Example 3 has further decreased the pH dependence of diltiazem release observed in Example 2 to indistinguishable levels.

Example 5

Figure 4:
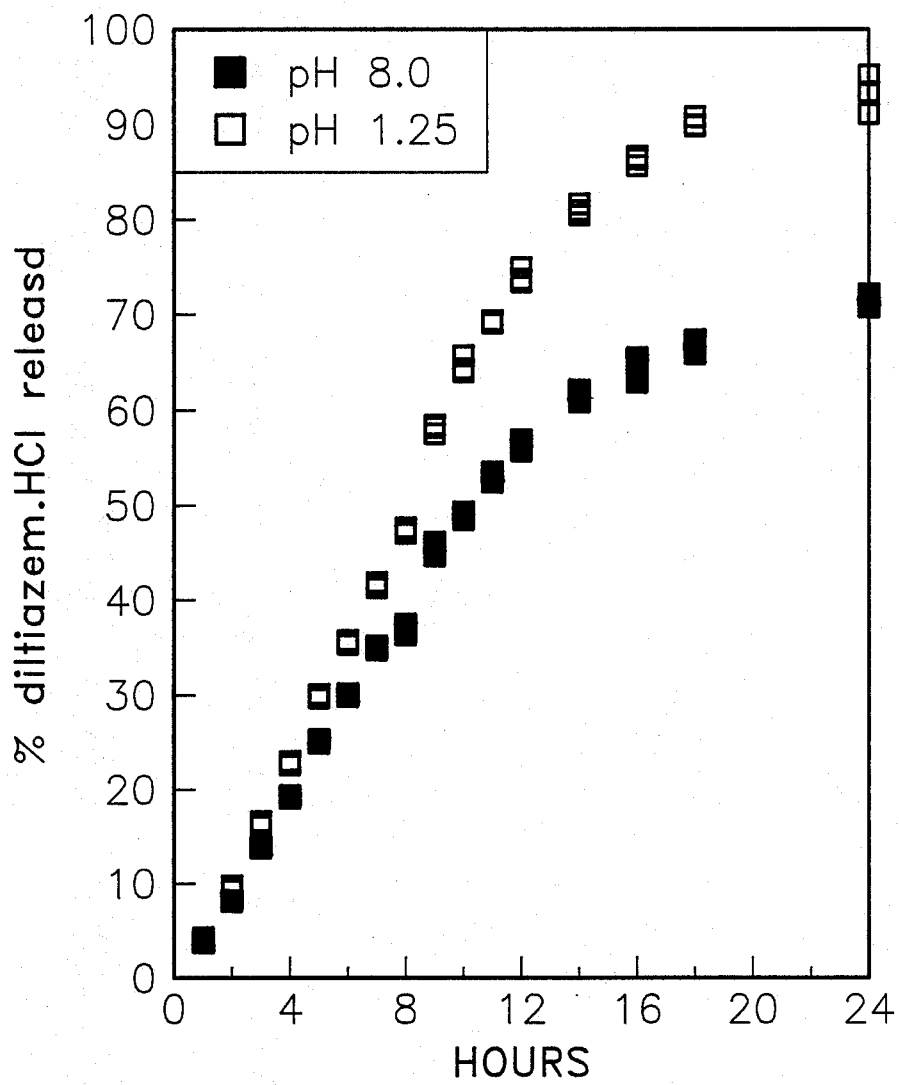
Figure 7:
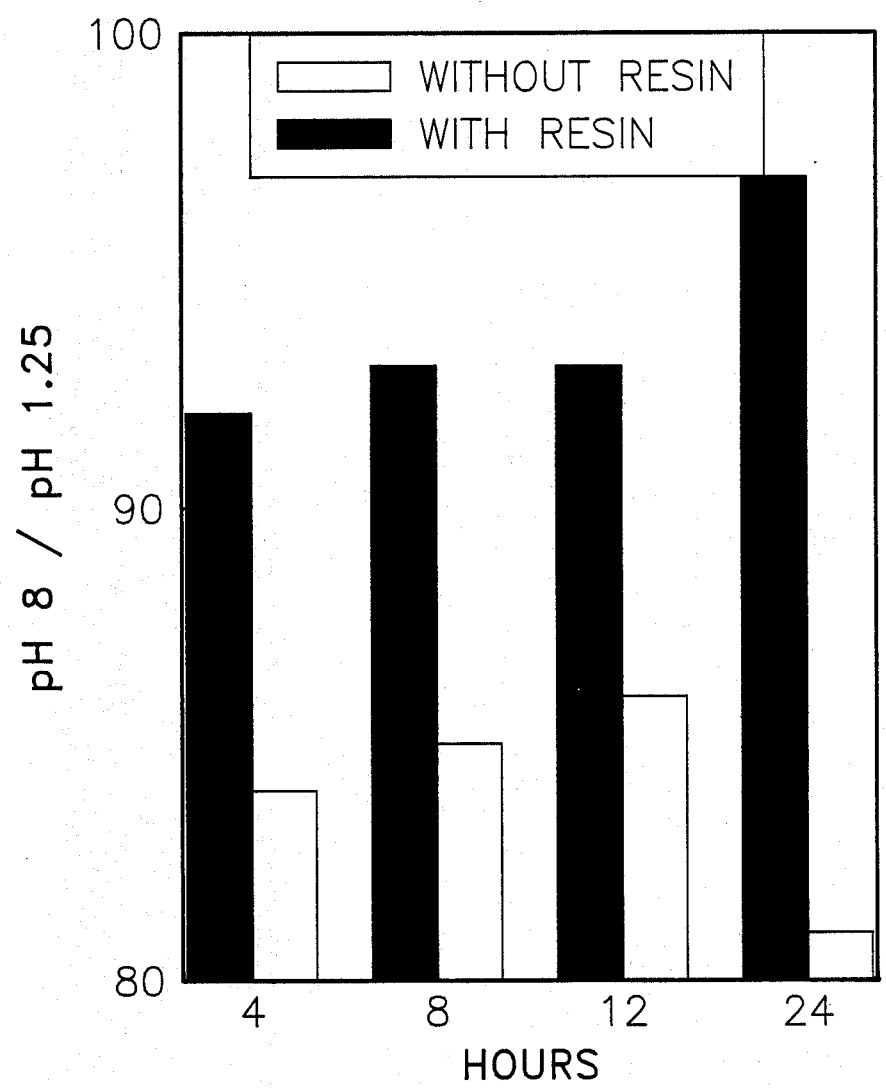

The 4, 8, 12 and 24 hour data points of FIGS. 4 and 6 are graphically compared in FIG. 7. The pronounced effects of the resins in promoting pH independent release are evident.

Figure 2:
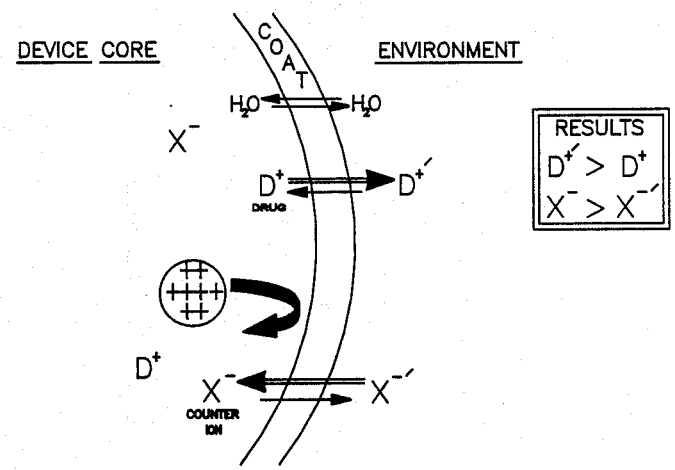

These conditions impose Donnan effects onto the release behavior of the drug from the device as illustrated in FIG. 2. Conditions of electrical neutrality dictate an unequal distribution of permeable charged species across a coat that is impermeable to a charged resin. This phenomena favors the movement of drug bearing a like change away from the resin, resulting in a modulation of the drug release normally associated with the mass transport effectuating concentration and osmotic gradients.

What is claimed is:

1. A drug-delivery device for the controlled release of a therapeutically active ingredient into an environment of use which comprises:
   (A) a core composition comprising
      (a) a water insoluble, non-diffusible charged resin entity, and (b) a diffusible water soluble ionizable therapeutically active ingredient carrying the same charge as said resin entity; and (B) a water insoluble wall surrounding said core composition and prepared from
  (i) a polymer material that is permeable to water but substantially impermeable to solute and
  (ii) 0.1 to 75% by weight, based on the total weight of (i) and (ii), of at least one water leachable pore forming additive dispersed throughout said wall.

2. A drug-delivery device according to claim 1, wherein the resin entity is a cationic resin selected from the group consisting of polystyrene, epoxy-amine, phenolic or condensate polymeric backbones containing an active group of quaternary ammonium, secondary amine, tertiary amine in an aromatic matrix or tertiary amine in an aliphatic matrix.

3. A drug-delivery device according to claim 1, wherein the resin entity is n anionic resin with acrylic, methacrylic or phenolic polymeric backbones with phosphonic acid or carboxylic acid active groups.

4. A drug-delivery device according to claim 1, wherein the resin entity is an anionic resin with polystyrene or phenolic polymeric backbones containing an active group of sulfonic acid.

5. A drug-delivery device according to claim 1, wherein the resin entity is a cellulose polymer selected from the group consisting of diethylaminoethyl cellulose, carboxymethyl cellulose, guanidoethyl cellulose, sulfoethyl cellulose, and sulfopropyl cellulose.

6. A drug-delivery device according to claim 1, wherein the resin entity is a cross-linked vinyl pyridine polymer.

7. A drug-delivery device according to claim 1, wherein the therapeutically active ingredient is soluble in an external fluid and exhibits an osmotic pressure gradient across the wall against the external fluid.

8. A drug-delivery device according to claim 1, wherein the therapeutically active ingredient has limited solubility in the external fluid and is mixed with an osmotically effective solute that is soluble in the fluid, which exhibit an osmotic pressure gradient across the wall against the external fluid.

9. A drug-delivery device according to claim 8, which further comprises in the core a member selected from water soluble excipients, buffers, insoluble buffers, bulking agents, and osmotic regulators.

10. A drug-delivery device according to claim 1, wherein said pore forming additive comprises:
  (a) 0.1 to 50%, by weight, solid additive, based on the total weight of (i) and (ii), and/or
  (b) 0.1 to 40%, by weight, liquid additive, based on the total weight of (i) and (ii), not to exceed a total weight % of pore forming additive of 60%.

11. A drug-delivery device according to claim 10, wherein 0.1 to 50%, by weight, of said pore forming additive is used.

12. A drug-delivery device according to claim 11, wherein said pore forming additive is selected from the group consisting of water, alkali metal salts, alkaline earth metal salts, saccharides, aliphatic polyols, aromatic polyols, nicotinamide and mixtures thereof.

13. A drug-delivery device according to claim 12, wherein said pore forming additive is selected from the group consisting of polyethylene glycol, sorbitol, glucose and mixtures thereof.

14. A drug-delivery device according to claim 1, further comprising:
  (C) 0 to 50 parts per 100 parts of (i) and (ii) of plasticizer and flux regulating additives and
  (D) 0 to 40 parts per 100 parts of (i) and (ii), of surfactant additive.

15. A drug-delivery device according to claim 1, wherein said water insoluble wall is 1 to 1,000 microns thick and wherein 5 to 95% of the resulting wall pores are between 10 angstroms and 100 microns in diameter.

16. A drug-delivery device according to claim 15 wherein said wall is 20 to 500 microns thick and said wall pores are between 10 angstroms and 25 microns in diameter.

17. A drug-delivery device according to claim 1, wherein at least 0.05 ng of active agent are used.

18. A drug-delivery device according to claim 17, wherein at least 1 microgram of active agent is used.

19. A drug-delivery device according to claim 1, wherein said polymer is selected from the group consisting of cellulose esters, acylated polysaccharides, polyurethane, polymers of acrylic and methacrylic acid and esters thereof, poly(ortho ester)s, polyacetals and mixtures thereof.

20. A drug-delivery device according to claim 19, wherein said polymer is selected from the group consisting of cellulose esters and acylated polysaccharides.

21. A drug-delivery device according to claim 20, wherein said polymer is selected from the group consisting of polyurethanes and polymers of acrylic and methacrylic acid and esters thereof.

22. A drug-delivery device according to claim 20, wherein said polymer is selected from the group consisting of poly(ortho ester)s and polyacetals.

* * * * *